United States Patent [19]

Sallee et al.

[11] Patent Number: 4,640,726
[45] Date of Patent: Feb. 3, 1987

[54] HEAT ACTIVATION PROCESS AND APPARATUS FOR HEAT SHRINKABLE MATERIAL

[75] Inventors: Lorry F. Sallee, Pine River; Robert L. Popp, Hortonville, both of Wis.

[73] Assignee: Kimberly-Clark Corporation, Neenah, Wis.

[21] Appl. No.: 749,170

[22] Filed: Jun. 27, 1985

[51] Int. Cl.$^4$ ............................................. B32B 31/26
[52] U.S. Cl. ......................................... 156/85; 156/86; 156/497; 156/499; 53/441; 53/442; 53/557; 34/210; 34/212; 34/215; 34/216; 34/217; 34/219; 34/223; 34/224; 34/225
[58] Field of Search ............... 156/84, 85, 86, 497, 156/499; 53/441, 442, 557; 34/22, 26, 28, 29, 210, 212, 215, 216, 217, 229, 223, 224, 225

[56] References Cited

U.S. PATENT DOCUMENTS

| | | | |
|---|---|---|---|
| 3,115,735 | 12/1963 | Harrison | 53/184 |
| 3,197,940 | 8/1965 | Spangler | 53/329 |
| 3,245,407 | 4/1966 | Mason | 128/284 |
| 3,309,789 | 3/1967 | Denker | 34/225 |
| 3,312,811 | 4/1967 | Shanklin | 219/388 |
| 3,347,013 | 10/1967 | Piazze | 53/30 |
| 3,357,153 | 12/1967 | Shaffer | 53/557 |
| 3,402,475 | 9/1968 | Johansen et al. | 34/23 |
| 3,430,358 | 3/1969 | Denker | 34/222 |
| 3,639,917 | 2/1972 | Althouse | 2/270 |
| 3,678,516 | 7/1972 | Backer | 2/224 |
| 3,717,939 | 2/1973 | Mitchell | 53/557 |
| 3,744,146 | 7/1973 | Nichols | 53/557 |
| 3,775,222 | 11/1973 | Aspen et al. | 156/497 |
| 3,897,671 | 8/1975 | Higgins | 53/557 |
| 3,912,565 | 10/1975 | Koch et al. | 156/85 |
| 4,011,122 | 3/1977 | Ashcroft | 156/86 |
| 4,337,771 | 7/1982 | Pieniak et al. | 128/287 |
| 4,413,623 | 11/1983 | Pieniak | 604/365 |

Primary Examiner—Caleb Weston
Attorney, Agent, or Firm—Paul Yee

[57] ABSTRACT

A method and apparatus for heating selected portions of an article include transport means for moving the article into a heating compartment. Shroud means, which are disposed within the heating compartment and located adjacent to limited portion of the article, direct a stream of heated gas toward a marginal portion of this article. Supply means deliver a volume rate flow of heated gas to the shroud means, and discharge means remove a volume rate of exhaust gas flow from the heating compartment. The discharge means is constructed and arranged to provide a volume rate of exhaust gas flow from the heating compartment which is greater than the volume rate of heated gas flow supplied into the shroud means.

25 Claims, 5 Drawing Figures

HEAT ACTIVATION PROCESS AND APPARATUS FOR HEAT SHRINKABLE MATERIAL

FIELD OF THE INVENTION

The present invention pertains to a method and apparatus for heating selected portions of an article. More particularly, the present invention pertains to a method and apparatus for heat activating an elasticizable material located on the article.

BACKGROUND OF THE INVENTION

U.S. Pat. No. 4,413,623 issued Nov. 8, 1983 to H. A. Pieniak discloses a method and apparatus for laminating an elastic strip in the leg opening portions of a disposable diaper. In the method taught by Pieniak, a stretched elastic is intermittently adhered to a web substrate.

U.S. Pat. No. 4,337,771 issued July 6, 1982 to H. A. Pieniak, et al. discloses a disposable diaper which has an elastic waistband portion. The elastic waistband may include a heat-shrinkable film ribbon which becomes elastic and contracts when the ribbon is heated to a predetermined temperature. The film ribbon is secured to the diaper while the ribbon is in an inelastic state. A hot air blast can be employed to shrink the ribbon and impart elasticity thereto.

The following documents disclose articles to which a heat activated elastomeric material has been attached: U.S. Pat. No. 3,912,565 issued Oct. 14, 1975 to W. T. Koch, et al.; U.S. Pat. No. 3,639,917 issued Feb. 8, 1972 to V. E. Althouse; U.S. Pat. No. 3,245,407 issued Apr. 12, 1966 to A. R. Mason; and U.S. Patent No. 3,678,516 issued July 25, 1972 to L. N. Backer.

The following documents disclose devices for heat shrinking a wrapping material around a packaged article, such as bread or a tissue paper roll: U.S. Pat. No. 3,430,358 issued Mar. 4, 1969 to S. D. Denker; U.S. Pat. No. 3,309,789 issued Mar. 21, 1967 to S. D. Denker; U.S. Pat. No. 3,312,811 issued Apr. 4, 1967 to F. G. Schanklin; U.S. Pat. No. 3,347,013 issued Oct. 17, 1967 to T. E. Piazze; and U.S. Pat. No. 3,402,475 issued Sept. 24, 1968 to J. H. Johansen, et al.

The following documents disclose devices for heat shrinking a cover member onto a container: U.S. Pat. No. 3,197,940 issued Aug. 3, 1965 to S. A. Spangler; and U.S. Pat. No. 3,115,735 issued Dec. 31, 1963 to J. W. Harrison.

Conventional devices, such as those taught by the above referenced documents, have not been completely satisfactory for heating selected, limited portions of an article, such as the marginal waistband portions of a garment, for example a disposable diaper. The conventional devices can distribute an excessive amount of heat to the main body of the diaper, which is generally not targeted for heating. In addition, the conventional heating devices can excessively heat the mechanical components of the apparatus and cause excessive maintenance requirements.

BRIEF DESCRIPTION OF THE INVENTION

The present invention provides an improved apparatus for heating a selected portion of an article. Generally stated, the apparatus includes transport means for moving the article into a heating compartment. Shroud means, disposed within the heating compartment and located adjacent to the article, direct a stream of heated gas toward a selected portion thereof. Supply means deliver a volume rate flow of the heated gas to the shroud means, and discharge means remove a volume rate of exhaust gas flow from the heating compartment. In a particular aspect of the invention, the discharge means is constructed and arranged to provide a volume rate of exhaust gas flow from the heating compartment which is greater than the volume rate of heated gas flow supplied into the shroud means.

The present invention further provides an efficient method for heating selected portions of an article which includes the step of moving the article into a heating compartment. A flow stream of heated gas is shrouded within the heating compartment and directed toward the selected portion of the article. A volume rate flow of heated gas is supplied into the shrouded gas stream, and a volume rate of exhaust gas flow is removed from the heating compartment. The volume rate of exhaust gas flow from the heating compartment is adjusted to be greater then the volume rate of heated gas flow supplied into the shrouded gas stream.

The method and apparatus of the present invention effectively heat selected target areas of an article while avoiding excessive heating of other areas. As a result, the present invention can efficiently activate a heat shrinkable elastomeric material. The invention advantageously restricts the volume of heated space, and can draw cooling air to minimize excessive heating of mechanical components and non-target areas of the article. Since the invention can efficiently recycle hot air, it can reduce the energy required for heat activating the elastomeric material. If desired, hot air can be diverted away from the heating compartment and away from the article located therein to minimize excessive heating or damage to the articles or to the manufacturing equipment.

BRIEF DESCRIPTION OF THE DRAWINGS

The invention will be more fully understood and further advantages will become apparent when reference is made to the following detailed description of the invention and the drawings in which.

DETAILED DESCRIPTION OF THE INVENTION

The present invention provides an improved method and apparatus for heating selected portions of a article, such as a disposable diaper, a disposable incontinence garment or an elasticized cuff on a gown. The invention is particularly suited for heat activating a heat shrinkable material to provide an elasticized portion of the article. For example, the heat shrinkable material may be positioned to provide an elasticized waistband of a disposable diaper or incontinence garment. Alternatively, the heat shrinkable material may be positioned to provide an elasticized head band on a cap or an elasticized cuff on a glove or disposable gown.

While the method and apparatus of the present invention will be further described in the context of a disposable diaper, it will be readily apparent that the invention can be employed in the manufacture of various types of articles, all of which are contemplated as being within the scope of the present invention.

Generally stated, a disposable diaper is comprised of a liquid permeable inner liner, a liquid impermeable outer layer, and an absorbent batt secured therebetween. The inner liner may be any soft, flexible porous sheet which passes fluids therethrough, and may be comprised of a nonwoven web or sheet of polyolefin fibers, such as polypropylene, wet strength tissue paper, a spunwoven filament sheet, or the like. The liquid impermeable outer layer may be comprised of a thin web or sheet of plastic film, such as polyethylene, polypropylene, polyvinylchloride or the like. The absorbent batt may be comprised of any suitable absorbent material. Typically, the batt is comprised of a cellulosic material, such as an air-formed batt of wood pulp fiber commonly known as "fluff".

The inner liner, outer layer and batt may be combined with one another in any suitable manner to form the finished diaper. For example, the elements may be bonded to one another by means of strips of patterns of hot melt or pressure sensitive adhesive, by patterned heat sealing, by strips of double faced pressure sensitive adhesive tape, or the like.

The diaper is generally "hour-glass" or I-shaped with a central narrowed crotch section and waistband sections located at each longitudinal end thereof. Elongate elastic means are secured in place adjacent the absorbent batt and on each side thereof to develop gathered elastic leg portions which are conformable with an infant's legs. In addition, the waist band sections may also have elongate elastic means incorporated therein to provide elasticized waist portions which are conformable with an infant's waist. Conventional pressure sensitive tapes are attached to the waistband sections to allow securement of the diaper around the infant.

The conformable waistbands of the diaper are typically manufactured by securing an elasticizable ribbon onto the diaper waistband while the ribbon is in a nonelastic state. After the elasticizable ribbon material has been affixed to the diaper waist section, the ribbon is later heat activated to shrink the ribbon and to convert the ribbon into an elasticized state. As a result, when the diaper is placed on an infant, the elastic waistband advantageously improves the fit of the diaper on the infant and reduces the leakage of fluids.

Figure 1:
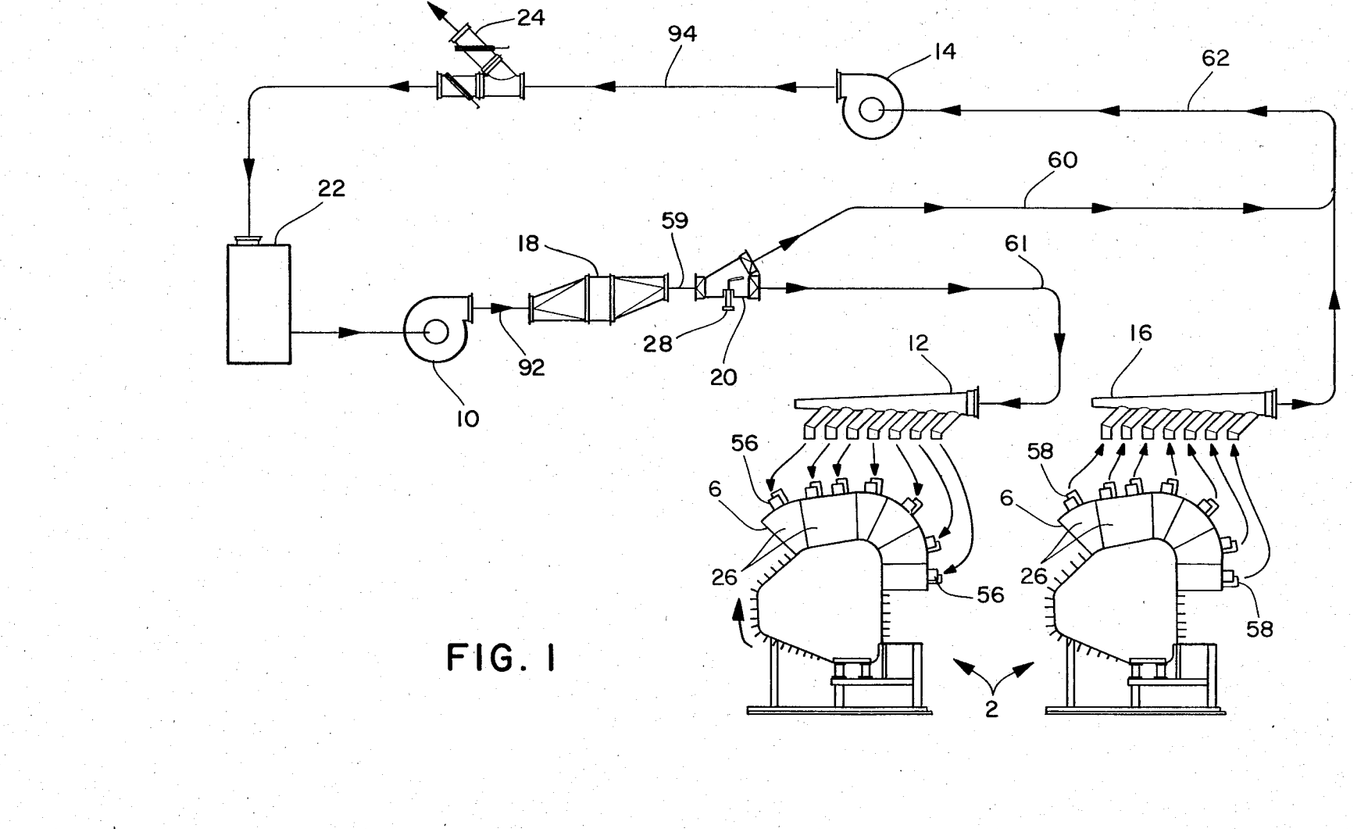
FIG. 1 representatively shows a schematic of the gas flow through the apparatus of the invention.
Figure 3:
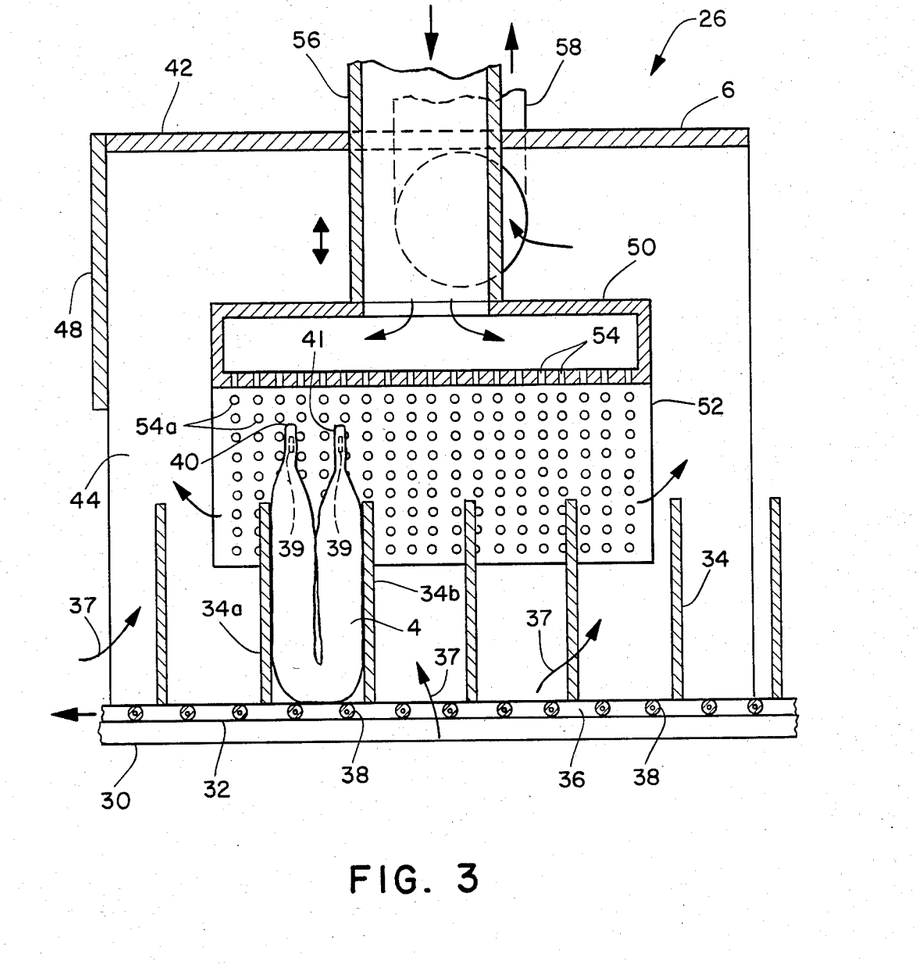
FIG. 3 representatively shows a cross-sectional side view of the heating compartment shown in FIG. 2.

The device of the present invention, as representatively shown in FIGS. 1 and 3, provides an effective apparatus for heating selected, limited portions of a disposable diaper. More particularly, the device provides an improved means for heat activating an elasticizable ribbon or strip located on the marginal, waistband sections of the diaper. The apparatus includes transport means, such as stacker 2, for moving disposable diaper 4 into a heating compartment 6. For the purposes of illustration and clarity, stacker 2 is shown in duplicate. Shroud means 8 is located within heating compartment 6, and is constructed for location adjacent to limited marginal portions of the article to direct a stream of heated gas toward those portions of the article. Supply means, comprised of activation fan 10 and supply header 12, deliver a volume flow rate of heated gas into the shroud means. Discharge means comprised of evacuation fan 14 and exhaust header 16 remove a volume flow rate of exhaust gas from heating compartment 6. The discharge means is constructed and arranged to provide a volume rate of exhaust gas flow from heating compartment 6 which is greater than the volume rate of heated gas flow supplied into shroud means 8.

As representatively shown in FIGS. 1 and 3, stacker 2 includes an articulated carrying means 32 which moves on a mechanical track 30. Track 30 forms a curvilinear, closed-looped circuit substantially around the periphery of stacker 2. Articulated carrier 32 is constructed with carrier segments 36 which are pivotable about pivot members 38. The pivotable segments allow the carrier to follow the curvature of track 30 as carrier 32 moves around the track circuit. Suitable driving means, such as an electrical motor (not shown), moves carrier 32 around track 30.

An array of substantially rigid fingers or paddle-like extensions 34 connect to carrier segments 36. Paddles 34 extend away from track 30 and are positioned generally perpendicular thereto. The paddles are regularly spaced along carrying means 32 and are configured to hold a selected article, such as folded diaper 4, therebetween.

With reference to FIG. 3, diaper 4 is oriented with its front and rear waistband portions 40 and 41, respectively, positioned away from carrier 32. Adjacent paddles 34a and 34b hold diaper 4 in a folded position, but leave waistband sections 40 and 41 in a substantially unrestrained condition.

Carrier 32 moves diaper 4 into a heating zone within heating compartment or "bonnet" 6 delimited by top wall 42, two side walls 44, bottom wall sections 46 and end wall sections 48. End walls 48 have apertures therethrough which are sized and configured to allow the passage of carrier 32, paddles 34 and diaper 4. Thus, compartment 6 effectively forms an enclosure around diaper 4 as it is moved therein by carrier 32. This enclosure substantially prevents an excessive loss of heated air to the surrounding environment.

As representatively depicted in FIG. 3, shroud means 8 is located within heating chamber 6, is constructed separate from the heating chamber walls and is configured for location adjacent and proximate to selected, limited portions of diaper 4. In particular, shroud 8 provides a baffle structure constructed for location in adjacent proximity to marginal waist band portions 40 and 41 of the diaper. The shroud is arranged to generally restrict the heating to the targeted waist band portions, and helps minimize any excessive heating of non-targeted portions.

Figure 2:
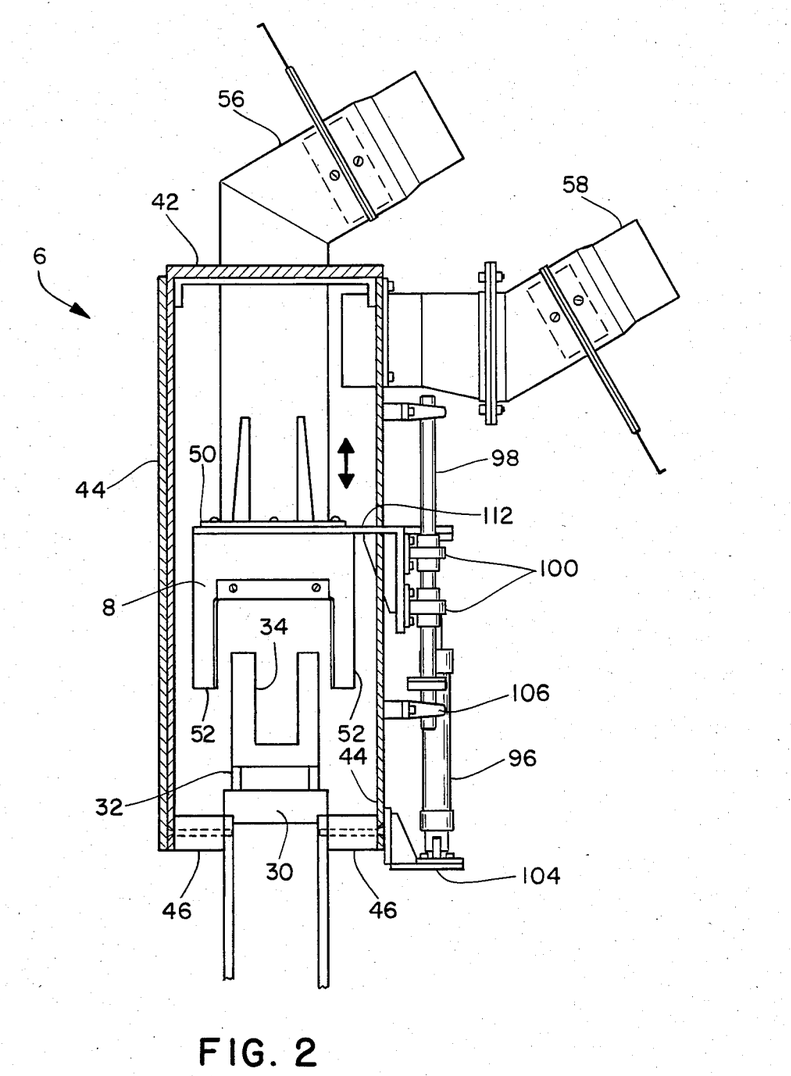
FIG. 2 representatively shows an end view into the heating compartment of the apparatus.

With reference to FIGS. 2 and 3, shroud 8 includes a cover conduit means 50 and two side conduit means 52. The side and cover conduits have gas passages therethrough for conducting heated gas from shroud inlet conduit 56, out through jet openings 54 and toward diaper 4. Cover conduit 50 is constructed for location adjacent and proximate to the top edge of marginal portions 40 and 41. The cover conduit has a plurality of jet openings 54 extending through an inwardly facing surface thereof that faces toward the location of diaper 4. At least one side conduit 52 is constructed and configured for location adjacent and proximate to a side edge of marginal portions 40 and 41. The side conduit has a plurality of jet openings 54a extending through an inwardly facing surface thereof that faces toward the position of diaper 4. This arrangement defines a restricted spatial volume within chamber 6 that is directly heated by the hot gas streams.

In a particular embodiment of the invention, two shroud sides 52 connect to opposite edge portions of shroud cover 50. The gas passages of the shroud cover are in fluid communication with the gas passages in the shroud sides, and the interconnected shroud cover and sides form a generally U-shape baffle structure that substantially surrounds three side edges of the diaper waistband portions 40 and 41. Side baffles 52 extend only part way down the side edges of diaper 4, and direct their hot gas streams essentially away from the main body of the diaper. The plurality of jet openings 54 are located on and distributed over the inwardly facing surfaces of the baffle structure. As a result, a plurality of heated gas streams can be directed toward diaper 4 at a plurality of angles relative to the marginal waist portions 40 and 41. The gas streams can advantageously interact to provide a turbulent and swirling gas flow that produces a fluttering movement of the waist portions and allows a more efficient penetration of heated air in between the waist portions to activate elasticizable waistband strips 39.

To increase the residence time of diaper 4 within the heating zone, heating compartment 6 can be configured as a series of heating cells 26 arranged end-to-end, as representatively shown in FIG. 1. By employing a series of cells, heating compartment 6 is more readily conformed to the curved path followed by carrier 32. As shown in FIG. 3, each cell 26 has an individual shroud means 8 located therein, as well as an individual inlet conduit 56 and an individual outlet conduit 58. This arrangement can advantageously allow a more uniform distribution of heated air throughout the series of cells. Suitable adjustments can be made to balance the amounts of heated air provided into the individual cells 26. Alternatively, heated air at selected, different temperatures can be supplied to individual, selected cells.

Supply means for delivering a volume rate of heated gas flow into baffle shroud 8 includes an activation fan 10 which draws a flow of air from filter box 22 and forces it through a heat exchanger having an air heater coil 18. Air heater coil 18 heats the gas to a temperature required to activate the elasticizable strip, typically within the range of about 65°–135° C., and directs the hot gas to air diverter valve 20 by way of conduit 59, as representatively shown in FIG. 1. Diverter valve 20 can be selectively engaged by way of control means 28 to direct the hot gas into supply header 12 or through bypass conduit line 60, which connects to exhaust conduit line 62. The diverter valve allows a rerouting of heated gas away from stacker heating compartment 6 if some problem develops with the stacker or the stacker transport mechanisms. For example, if a group of diapers should plug stacker 2, the hot air could damage the equipment or the diaper products unless it is redirected through bypass line 60. In addition, during the start-up mode, the hot air can be bypassed around stacker 2 and recirculated through air heater coil 18 to reduce energy consumption and to reduce the time required to bring the heated air up to the desired temperature.

During normal production operations, air diverter valve 20 direct hot air into supply header 12 by way of conduit 61. The supply header directs the hot air into the various inlet conduits 56 leading into heating cells 26. In a typical configuration, the volume flow rate of hot gas in through conduits 56 ranges from about 1500–4000 cfm (about 0.71–1.89 m$^3$/sec). It is readily appreciated, however, that the temperature of the heated gas and the flow rate of the gas are adjusted as required to thermally activate the elasticizable material on the waist portions of diaper 4.

Figure 5:
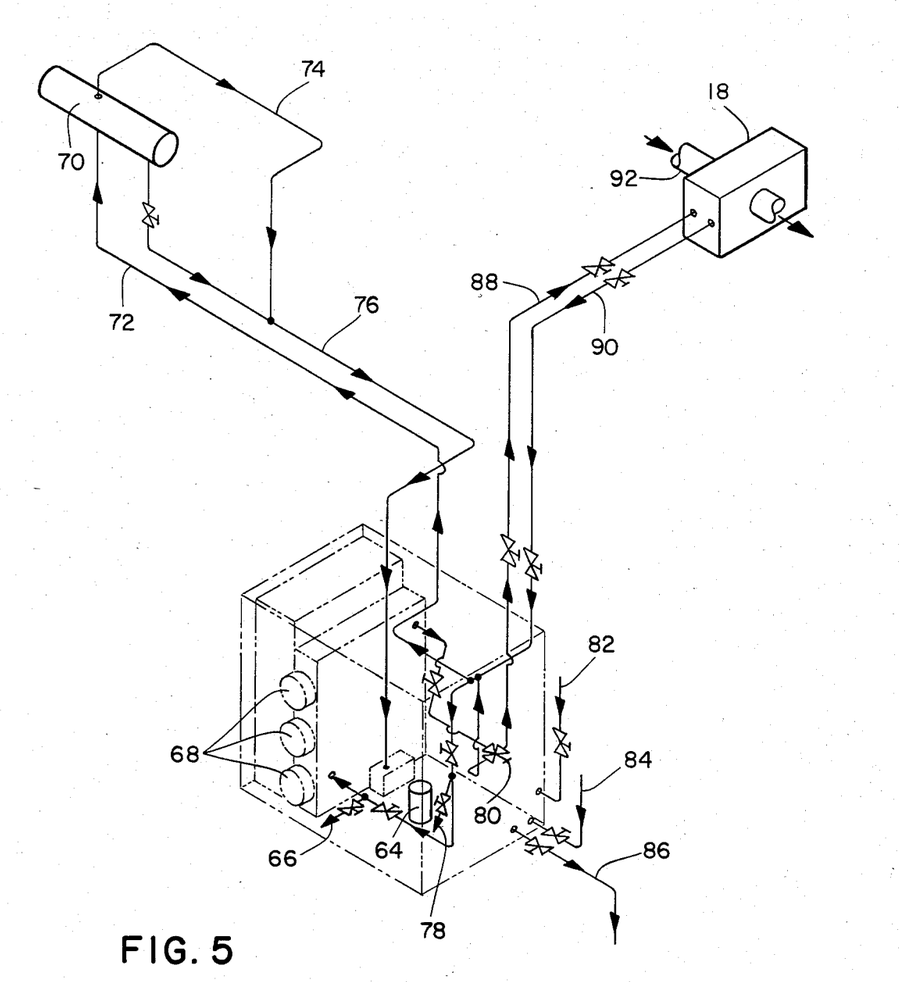
FIG. 5 representatively shows a schematic of the hot liquid system employed to heat the gas directed into the heating compartment.

FIG. 5 representatively shows a detailed schematic of a heating means for heating the gas passing through air heater coil 18. The heating means can generally be described as a heat exchanger, and includes a liquid heating means 68 for heating a circulating liquid, such as ethylene glycol. Liquid reservoir means, such as expansion tank 70 supplies a volume of liquid glycol through lines 74 and 76, and a liquid supply conduit, such as glycol supply line 88, conducts the heated glycol from glycol heater 68 to a suitable heat exchanging conduit network, such as air heater coil 18. A liquid return conduit, such as glycol return line 90, conducts the glycol from air heater coil 18 to glycol heater 68. Directing means, such as air conduit 92, guides the input gas flow from activation fan 10 through air heater coil 18 to heat the gas.

The glycol heat transfer system shown in FIG. 5 is designed to supply a sufficient quantity of hot glycol liquid into air heater coil 18. Centrifugal pump 64 drives and transports the glycol through the entire system. In particular, the glycol is pumped directly into three heaters 68 in which the glycol is heated to a temperature near 400° F. (204° C.) and transferred toward a three-way diverter valve 80.

At diverter valve 80, a number of different events may take place. First, the glycol may be completely diverted back through the pump and into the heaters 68. This most commonly occurs during initial start-up of the unit, and allows the system to bring the circulating glycol up to the proper temperature and flow rates.

Secondly, the glycol can be completely directed to air heating coil 18 by way of glycol supply line 88. In this situation, glycol enters air heater coil 18 at a rate of about 10–120 gallons per minute. Air or any other suitable gas is forced passed air heating coils 18 through conduit 92 by activation fan 10. This process heats the air to a temperature of about 230° F. (110° C).

Finally, in a third situation which most commonly occurs, the three-way diverter valve 80 is controlled by sensors, controllers and an actuator which proportionately adjusts the flow of glycol to either air heating coil 18 or back into glycol heaters 68. This heat transfer control unit can thereby constantly maintain a balance of fluid flow, pressure and temperature in the device.

Expansion tank 70 stores any excess volume of glycol fluid. Since heated glycol does expand, the expansion tank provides an additional volume to accommodate this expansion through line 72 and prevents bursting of the pipe connections. In addition, expansion tank 70 serves as reservoir to store an extra capacity of glycol.

Strainer 78 filters out any particulates, such as weld, slags, dirt and metal shavings, which may have been trapped within the unit. Fill port 66 provides an inlet for initially filling the system with glycol. Compressed air inlet line 82 supplies compressed air at about 80–100 psi (about 551.6–689.5 kPa) to activate the pneumatic components, such as three-way diverter valve 80. Cooling water inlet line 84 provides cooling water to the pump at a rate of about 1–3 gallons per minute to prevent over heating of the pump. The spent cooling water is removed through water drain line 86.

Referring again to FIGS. 1 and 2, an exhaust outlet conduit 58 is connected in fluid communication with each cell of heating compartment 6, and evacuation fan 14 connects in fluid communication with exhaust conduit 62 to provide a volume rate of exhaust gas flow therethrough. Return conduit 94 connects in fluid communication with the recirculation bypass valve 24 and exhaust conduit 62.

Although activation fan 10 and evacuation fan 14 are similar, the functions performed by each are somewhat different. In particular, activation fan 10 forces hot air into and through shroud 8, but evacuation fan 14 pulls air out and away from heating bonnet 6. In addition, evacuation fan 14 is constructed and configured to draw out a volume rate of exhaust gas flow which exceeds the volume rate of heated gas flow provided by activation fan 10. For example, the volume rate of exhaust gas flow can be adjusted to exceed the volume rate of heated, input gas flow by about 500 cfm (about 0.236 m$^3$/sec). This difference in gas flows advantageously provides a significant volume rate of cooling air flow 37 from the ambient atmosphere past the main portion of diaper 4 and past the mechanical components of stacker 2. This flow of cooling air minimizes excessive heating of the non-target portions of the diapers and stacker components.

As described above, the volume of return, exhaust air is greater than the volume of supply, input air. As a result, it is necessary to bleed out a portion of this excess air volume through recirculation bypass valve 24 before the recirculated air volume is directed back into activation fan 10. A manually operated dampening system, for example, can be employed to adjust and regulate the quantity of air flow through bypass valve 24.

Filter box 22 prevents dust-laden air from entering the activation fan and being blown onto the air heating coils 18. Without filter box 22, the dust build up would decrease the efficiency of the air heating coils.

Figure 4:
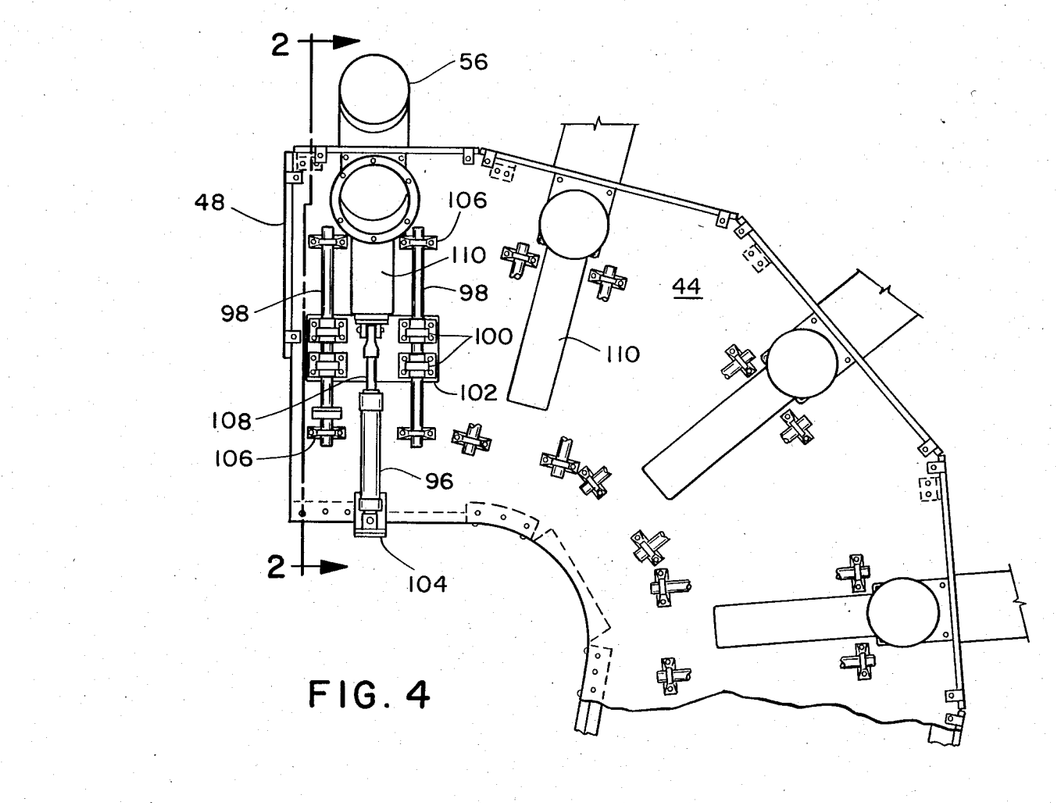
FIG. 4 representatively shows a side, plan view of the actuator device employed to move the shroud means within the heating compartment.

A further aspect of the invention includes an actuator means, such as pneumatic actuator 96, for selectively moving shroud 8 toward or away from the position of diaper 4 within heating bonnet 6. The actuator advantageously allows a movement of shroud 8 in a direction away from carrier 32 to allow the clearing of any plugging that may occur within stacker 2.

Referring to FIGS. 2 and 4, actuator support 104 rigidly connects actuator 96 to the stacker apparatus. Actuator rod 108 extends and retracts to operably drive plate member 102. Suitable fastening means interconnect rod 108 and drive plate 102. Drive plate 102 connects to a pair of substantially parallel guide rails 98 by means of slidable bearings 100 and 106. As actuator rod 108 moves, drive plate 102 moves along a track defined by rails 98. Arm 112 interconnects drive plate 102 and shroud 8. Thus, as drive plate 102 is moved along rails 98, arm 112 operably moves shroud 8 in the direction represented by the arrows, toward or away from the diaper position within heating compartment 6. A relief slot opening 110 extends through chamber side 44 to accommodate the free movement of drive arm 112.

It is readily apparent that the various components of the invention may be constructed from any suitable heat-resistant material. For example, the components may be constructed from various metals, heat resistant plastics and heat resistant composite materials.

Having thus described the invention in rather full detail, it will be readily apparent to a person having ordinary skill in the art that various changes and modifications may be made without departing from the spirit of the invention. Such changes and modifications are all contemplated as being within the scope of the invention as defined by the subjoined claims.

We claim:
1. An apparatus for heating selected portions of an article, comprising:
   (a) transport means for moving said article into a heating compartment;
   (b) shroud means disposed within said heating compartment for directing a stream of heated gas toward a selected portion of the article;
   (c) supply means for delivering a volume rate of flow of said heated gas to said shroud means; and
   (d) discharge means for removing a volume rate of exhaust gas flow from said heating compartment, said discharge means constructed and arranged to provide a volume rate of exhaust gas flow from said heating compartment which is greater than the volume rate of heated gas flow supplied into said shroud means and to provide a cooling gas flow past article portions which are not targeted for heating.

2. An apparatus as recited in claim 1, wherein said shroud means is constructed and arranged to direct a plurality of heated gas streams toward an article marginal portion at a plurality of angles relative to said marginal portion to thereby provide a turbulent gas flow that produces a fluttering of said marginal portion.

3. An apparatus as recited in claim 1, wherein said shroud means comprises:
   (a) a cover conduit means constructed for location adjacent to a top edge of a marginal portion of said article and having a plurality of openings through an inwardly facing surface thereof; and
   (b) at least one side conduit means constructed for location adjacent to a side edge of said marginal portion of said article and having a plurality of openings through an inwardly facing surface thereof.

4. An apparatus as recited in claim 3, wherein said shroud means comprises two side conduit means connected to said cover conduit means to provide a generally U-shaped conduit assembly.

5. An apparatus as recited in claim 1, wherein
   (a) said supply means includes an activation fan for providing a volume rate of heated input gas flow into said shroud means;
   (b) said discharge means includes an evacuation fan for providing a volume rate of exhaust gas flow from said heating compartment; and
   (c) said evacuation fan is constructed and arranged to provide a volume rate of exhaust gas flow which is greater than the volume rate of input gas flow provided by said activation fan.

6. An apparatus as recited in claim 1, wherein said discharge means comprises:
   (a) an exhaust conduit connected in fluid communication with said heating compartment;
   (b) an evacuation fan connected in fluid communication with said exhaust conduit for providing a volume rate of exhaust gas flow therethrough;
   (c) a return conduit connected in fluid communication with said gas supply means and said exhaust conduit.

7. An apparatus as recited in claim 1, wherein said supply means comprises:
   (a) an activation fan for providing a volume rate of input gas flow;
   (b) heating means for heating said gas;

(c) a supply conduit for conducting said heated gas to said shroud means; and (d) a diverter located in said supply conduit for selectively directing said gas flow through said supply conduit means, or through a bypass conduit connected in fluid communication with an exhaust conduit.

8. An apparatus as recited in claim 7, further comprising control means for selectively engaging said diverter to selectively direct said gas flow through said supply conduit means or through said bypass conduit to said exhaust conduit.

9. An apparatus as recited in claim 7, wherein said heating means includes a heat exchanger, which comprises:

(a) liquid heating means for heating a circulating liquid;

(b) liquid reservoir means for supplying said circulating liquid;

(c) a liquid supply conduit for conducting heated liquid from said liquid heating means to a heat exchanging conduit network;

(d) a liquid return conduit for conducting liquid from said heat exchanging conduit network to said liquid heating means;

(e) directing means for guiding said input gas flow through said heat exchanging conduit network to heat said gas.

10. An apparatus as recited in claim 1, further comprising actuator means for selectively moving the position of said shroud means within said heating compartment.

11. An apparatus as recited in claim 10, wherein said actuator means is comprised of a pneumatic actuator.

12. An apparatus as recited in claim 1, wherein (a) said shroud means comprises,
 i. at least one cover conduit means constructed for location adjacent to a top edge of a marginal portion of said article and having a plurality of openings through an inwardly facing surface thereof, and
 ii. two side conduit means constructed for location adjacent to two side edges of said marginal portion of said article and having a plurality of openings through an inwardly facing surface thereof, said cover conduit means and said two side conduit means thereby configured to form a generally U-shaped structure;

(b) said discharge means comprises,
 i. an exhaust conduit connected in fluid communication with said heating compartment,
 ii. an evacuation fan connected in fluid communication with said exhaust conduit for providing a volume rate of exhaust flow therethrough, and
 iii. a return conduit connected in fluid communication with said gas supply means and said exhaust conduit; and (c) said supply means comprises,
 i. an activation fan for providing a volume rate of input gas flow,
 ii. heating means for heating said gas,
 iii. a supply conduit for conducting said input gas flow to said shroud means, and
 iv. a diverter located in said supply conduit means for selectively directing said gas flow through said supply conduit means or through a bypass conduit which is connected in fluid communication with said exhaust conduit.

13. An apparatus as recited in claim 12, wherein the volume rate of exhaust gas flow provided by said evacuation fan is greater than the volume rate of input gas flow provided by said activation fan.

14. An apparatus as recited in claim 1, wherein said shroud means defines within said heating compartment a restricted spatial volume which substantially surrounds selected, limited portions of said article and generally restricts said heated gas flow to limited target portions of said article.

15. A method for heating selected portions of an article, comprising the steps of:

(a) moving said article into a heating compartment;

(b) shrouding a flow stream of heated gas within said heating compartment to direct said heated gas stream toward selected, limited portions of said article;

(c) supplying a volume rate input flow of said shrouded flow stream of heated gas; and (d) removing a volume rate of exhaust gas flow from said heating compartment, said volume rate of exhaust gas flow from said heating compartment being greater than the volume rate input flow of said shrouded stream of heated gas and said volume rate of exhaust gas flow adjusted to provide a cooling gas flow past article portions which are not targeted for heating.

16. A method as recited in claim 15, further comprising the step of selectively diverting said shrouded flow stream of heated gas away from said heating compartment and into a bypass conduit.

17. A method as recited in claim 15, further comprising the step of selectively moving the position of said shrouded flow stream of heated gas within said heating compartment.

18. A method as recited in claim 15, further comprising the step of directing said shrouded flow stream of heated gas toward said selected article portion at a plurality of angles relative to said marginal portion to thereby provide a turbulent gas flow that produces a fluttering of said marginal portion.

19. A method as recited in claim 15, wherein said shrouding step (b) defines within said heating compartment a restricted spatial volume which substantially surrounds selected, limited portions of said article and generally restricts said heated gas flow to limited target portions of said article.

20. An apparatus for heating selected portions of an article, comprising:

(a) transport means for moving said article into a heating compartment;

(b) shroud means disposed within said heating compartment for directing a stream of heated gas toward a selected portion of the article;

(c) supply means for delivering a volume rate of flow of said heated gas to said shroud means; and (d) discharge means for removing a volume rate of exhaust gas flow from said heating compartment, said discharge means constructed and arranged to provide a volume rate of exhaust gas flow from said heating compartment which is greater than the volume rate of heated gas flow supplied into said shroud means, and said discharge means comprising,
 (i) an exhaust conduit connected in fluid communication with said heating compartment;
 (ii) an evacuation fan connected in fluid communication with said exhaust conduit for providing a volume rate of exhaust gas flow therethrough; and (iii) a return conduit connected in fluid communication with said gas supply means and said exhaust conduit.

21. An apparatus as recited in claim 20, wherein said supply means comprises:
   (a) an activation fan for providing a volume rate of input gas flow,
   (b) heating means for heating said gas,
   (c) a supply conduit for conducting said input gas flow to said shroud means, and
   (d) a diverter located in said supply conduit means for selectively directing said gas flow through said supply conduit means or through a bypass conduit which is connected in fluid communication with said exhaust conduit.

22. An apparatus as recited in claim 21, wherein said shroud means comprises:
   (a) at least one cover conduit means constructed for location adjacent to a top edge of a marginal portion of said article and having a plurality of openings through an inwardly facing surface thereof; and
   (b) two side conduit means constructed for location adjacent to two side edges of said marginal portion of said article and having a plurality of openings through an inwardly facing surface thereof, said cover conduit means and said two side conduit means thereby configured to form a generally U-shaped structure.

23. An apparatus for heating selected portions of an article, comprising:
   (a) transport means for moving said article into a heating compartment;
   (b) shroud means disposed within said heating compartment for directing a stream of heated gas toward a selected portion of the article;
   (c) supply means for delivering a volume rate of flow of said heated gas to said shroud means, wherein said supply means comprises,
      (i) an activation fan for providing a volume rate of input gas flow,
      (ii) heating means for heating said gas;
      (iii) a supply conduit for conducting said heated gas to said shroud means, and
      (iv) a diverter located in said supply conduit for selectively directing said gas flow through said supply conduit means, or through a bypass conduit connected in fluid communication with an exhaust conduit; and
   (d) discharge means for removing a volume rate of exhaust gas flow from said heating compartment, said discharge means constructed and arranged to provide a volume rate of exhaust gas flow from said heating compartment which is greater than the volume rate of heated gas flow supplied into said shroud means.

24. An apparatus as recited in claim 23, wherein said heating means includes a heat exchanger, which comprises:
   (a) liquid heating means for heating a circulating liquid;
   (b) liquid reservoir means for supplying said circulating liquid;
   (c) a liquid supply conduit for conducting heated liquid from said liquid heating means to a heat exchanging conduit network;
   (d) a liquid return conduit for conducting liquid from said heat exchanging conduit network to said liquid heating means;
   (e) directing means for guiding said input gas flow through said heat exchanging conduit network to heat said gas.

25. An apparatus as recited in claim 23, further comprising control means for selectively engaging said diverter to selectively direct said gas flow through said supply conduit means or through said bypass conduit to said exhaust conduit.

* * * * *